United States Patent
Hou et al.

(10) Patent No.: US 10,130,315 B2
(45) Date of Patent: Nov. 20, 2018

(54) SCANNING BED CONTROL APPARATUS OF MEDICAL IMAGING EQUIPMENT

(71) Applicant: SHENYANG NEUSOFT MEDICAL SYSTEMS CO., LTD., Shenyang (CN)

(72) Inventors: Guitang Hou, Shenyang (CN); Xiaojing Yun, Shenyang (CN); Wei Fang, Shenyang (CN); Guotao Zhao, Shenyang (CN)

(73) Assignee: Shenhang Neusoft Medical Systems Co., Ltd., Shenyang (CN)

( * ) Notice: Subject to any disclaimer, the term of this patent is extended or adjusted under 35 U.S.C. 154(b) by 161 days.

(21) Appl. No.: 15/277,945

(22) Filed: Sep. 27, 2016

(65) Prior Publication Data

US 2017/0164912 A1    Jun. 15, 2017

(30) Foreign Application Priority Data

Dec. 11, 2015    (CN) .......................... 2015 1 0926329

(51) Int. Cl.
*A61G 13/00*    (2006.01)
*A61B 6/04*    (2006.01)

(52) U.S. Cl.
CPC .......... *A61B 6/0457* (2013.01); *A61B 6/0471* (2013.01)

(58) Field of Classification Search
CPC ..................................... A61G 13/00
USPC ..................................... 5/601, 600
See application file for complete search history.

(56) References Cited

U.S. PATENT DOCUMENTS

| | | | |
|---|---|---|---|
| 4,641,823 A | * | 2/1987 | Bergman ............. A61B 5/0555 5/81.1 HS |
| 6,212,251 B1 | | 4/2001 | Tomura et al. |
| 6,381,780 B1 | | 5/2002 | Nose et al. |
| 7,621,007 B2 | | 11/2009 | Somasundaram |
| 2005/0204472 A1 | | 9/2005 | Gagneur et al. |
| 2006/0042009 A1 | * | 3/2006 | Somasundaram ... A61B 6/0457 5/601 |
| 2007/0226906 A1 | | 10/2007 | Farooqui |
| 2008/0235874 A1 | | 10/2008 | Grosshauser et al. |
| 2009/0172882 A1 | | 7/2009 | Farooqui |
| 2014/0187379 A1 | | 7/2014 | Chen et al. |

FOREIGN PATENT DOCUMENTS

| | | |
|---|---|---|
| CN | 201150539 Y | 11/2008 |
| CN | 102309321 A | 1/2012 |
| CN | 202776341 U | 3/2013 |

(Continued)

*Primary Examiner* — Fredrick C Conley
(74) *Attorney, Agent, or Firm* — McCoy Russell LLP

(57) ABSTRACT

The present disclosure provides a scanning bed control apparatus of medical imaging equipment. According to an example of the present disclosure, this scanning bed control apparatus comprises a support table and a drive mechanism connected between the support table and the scanning bed of medical imaging equipment. This drive mechanism comprises a drive motor, a central frame and a drive unit set on the central frame. Where, an output end of the drive motor is connected with a gear, and a rack joggled with the gear is fixed on the central frame. When the drive motor drives the central frame to move back and forth by joggle between the gear and the rack, the drive unit may proceed two-stage drive following the back and forth movement of the central frame.

18 Claims, 3 Drawing Sheets

(56) References Cited

FOREIGN PATENT DOCUMENTS

| | | |
|---|---|---|
| CN | 103027817 A | 4/2013 |
| CN | 202920183 U | 5/2013 |
| CN | 103263276 A | 8/2013 |
| CN | 103961132 A | 8/2014 |
| CN | 204744172 U | 11/2015 |
| WO | 0232310 A1 | 4/2002 |
| WO | 2004105603 A1 | 12/2004 |

* cited by examiner

SCANNING BED CONTROL APPARATUS OF MEDICAL IMAGING EQUIPMENT

CROSS-REFERENCE TO RELATED APPLICATIONS

The present application claims priority to Chinese Patent Application No. 201510926329.5, filed on Dec. 11, 2015, the entire contents of which are hereby incorporated by reference for all purposes.

BACKGROUND

The disclosure relates to a scanning bed control apparatus of medical imaging equipment.

In the diagnosis process of some diseases in patients, a variety of different imaging technologies may be used to scan and image the patients, so as to assist the diagnosis. Those imaging technologies comprise MRI (Magnetic Resonance Imaging), CT (Computed Tomography), PET (Positron Emission Tomography), etc., and relevant medical imaging equipment usually comprises a scanning bed to support the patient. The scanning bed may be controlled to move, thus to convey and locate the patient accurately.

The horizontal movement of double-deck scanning bed with three-stage drive may achieve scanning in a large scope. However, three-stage drive usually includes multiple driving sources to drive step by step, with high manufacturing cost.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF DRAWINGS

The details of one or more embodiments of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Figure 1:
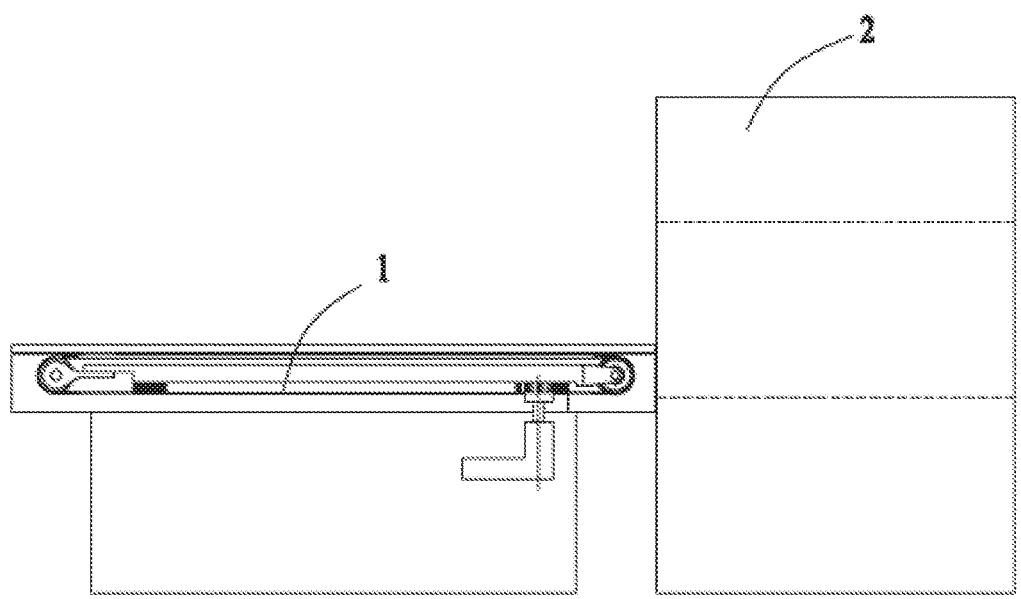
FIG. 1 is a structure diagram illustrating an initial state of a scanning bed in medical imaging equipment according to an example of the present disclosure.
Figure 2:
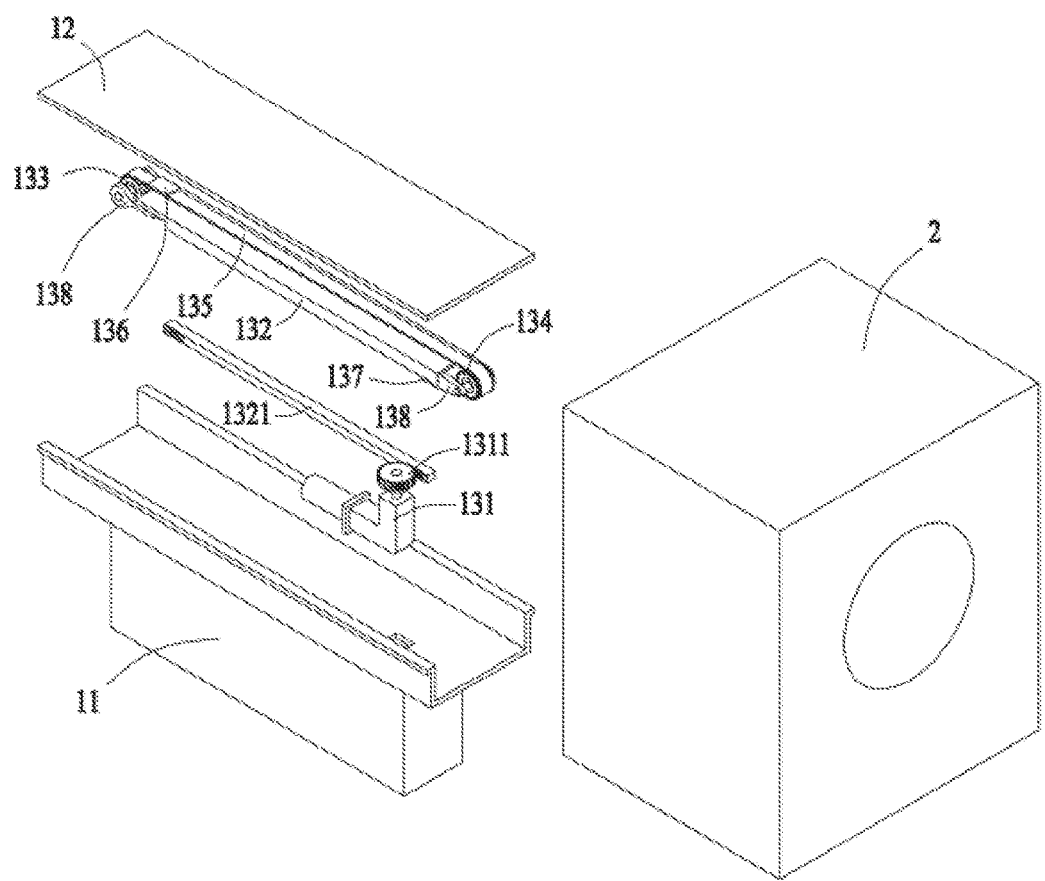
FIG. 2 is a structure diagram illustrating a deconstruction of a scanning bed control apparatus in medical imaging equipment according to an example of the present disclosure.
Figure 3:
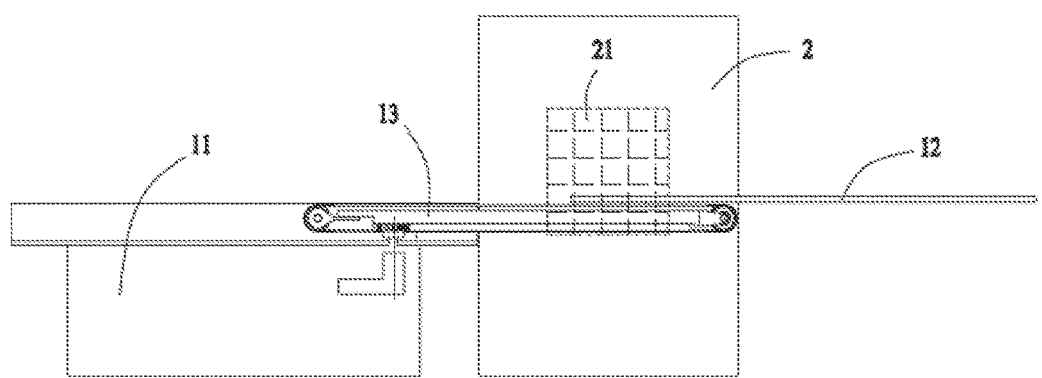
FIG. 3 is a structure diagram illustrating a scanning bed in medical imaging equipment at a maximum stroke position according to an example of the present disclosure.

As shown in FIG. 1, a structure diagram of an initial state of a scanning bed in medical imaging equipment according to an example of the present disclosure, is illustrated. As shown in FIGS. 1-3, the medical imaging equipment may comprise a scanning bed control apparatus 1, an imaging device 2 and a scanning bed 12. The scanning bed control apparatus 1 may include a support table 11 and a drive mechanism 13 connected between the support table 11 and the scanning bed 12. In some examples the drive mechanism 13 may realize a synchronized two-stage drive. For example, the drive mechanism 13 may realize a synchronized two-stage drive by one driving source. In this way, the structure of scanning bed control apparatus 1 may be simplified, transmission efficiency and transmission accuracy may be effectively improved, and manufacturing cost may be effectively reduced.

As shown in FIGS. 1-3, the drive mechanism 13 of this disclosure may comprise a drive motor 131, a central frame 132 and a drive unit (which is not marked). The drive unit may be set on the central frame 132, and it may be driven to rotate circularly in central frame 132. In some examples, the drive motor 131 may be an electric motor, or may comprise a combination of an electric motor and a speed reducer. An output end of the drive motor 131 may be connected with a gear 1311. Correspondingly, the central frame 132 may be fixed with a rack 1321 joggled with said gear 1311. In such an example, with joggle between the gear 1311 and the rack 1321, the drive motor 131 in rotating may drive the central frame 132 to move back and forth in the horizontal direction. When the central frame 132 moves back and forth, the drive unit may be driven by it for two-stage drive. As the scanning bed 12 may be set on the drive unit, the scanning bed 12 may move back and forth in the horizontal direction following the drive unit.

In particular, the drive unit may comprise a first driving wheel 133, a second driving wheel 134, a conveyor belt 135 as well as a first connector 136 and a second connector 137 set on the driving belt 135. In some examples, the first driving wheel 133 and the second driving wheel 134 may be set on two ends of the central frame 132, respectively. Correspondingly, the two ends of the central frame 132 may comprise a driving wheel support 138 respectively. According to an example, the driving wheel support 138 may be U-shaped. In such an example, the first driving wheel 133 and the second driving wheel 134 may be set in the U-shaped space of the driving wheel supports 138, and fixed on the driving wheel support 138 through a rotation axis or a hinge pin. Thus, the first driving wheel 133 and the second driving wheel 134 may move together with corresponding hinge pin or may rotate along the axis of the rotation axis. The conveyor belt 135 may be sleeved on the first driving wheel 133 and the second driving wheel 134, to drive conveyor belt 135 to rotate circularly through the synchronous rotation of the first driving wheel 133 and the second driving wheel 134.

Since the conveyor belt 135 is closed from head to tail in a ring shape, and sleeved between the first driving wheel 133 and the second driving wheel 134, as shown in FIG. 2, the conveyor belt 135 may be divided into two layers by the first driving wheel 133 and the second driving wheel 134. The first connector 136 may be set on the upper layer of the conveyor belt 135 to connect with the scanning bed 12, and the second connector 137 may be set on the lower layer of the conveyor belt 135 to connect with the support table 11. In this disclosure, the first connector 136 and the second connector 137 may be controlled to move back and forth between the first driving wheel 133 and the second driving wheel 134. As an example, the first connector 136 may move back and forth on the upper layer of the conveyor belt 135, while the second connector 137 may move back and forth on the lower layer of the conveyor belt 135.

In one example, the rack 1321 may be horizontally fixed on the side of the central frame 132, the gear 1311 may be fixed on an output end of the drive motor 131, and the drive motor 131 may drive the central frame 132 to move back and forth through the cooperation of the rack 1321 and the gear 1311. When the central frame 132 moves back and forth, the drive unit set on the central frame 132 may move back and forth together with it. In addition, as the second connector 137 on the conveyor belt 135 may connect with the support table 11, the conveyor belt 135 may be driven to transmit on the central frame 132 when the central frame 132 is driven to move back and forth. In this way, the conveyor belt 135 may take the connection point between the second connector 137 and the support table 11 as a fixed point, to drive the scanning bed 12 to move back and forth between the first driving wheel 133 and the second driving wheel 134. Thus, it may realize synchronized two-stage drive by one driving source, make the scanning bed 12 to reach the maximum stroke, so as to transfer the patient into a scanning area 21 of the imaging device 2.

According to another example, the first connector 136 and the second connector 137 may set on opposite sides of the conveyor belt 135. For example, when the scanning bed 12 is at an initial position, the first connector 136 may be close to the first driving wheel 133, and the second connector 137 may be close to the second driving wheel 134; and, when the scanning bed 12 reaches a maximum stroke, the first connector 136 may be close to the second driving wheel 134, and the second connector 137 may be close to the driving wheel 133. In an example of the present disclosure, the first driving wheel 133 and the second driving wheel 134 may be synchronous pulleys, and the conveyor belt 135 may be a synchronous belt. In another example of the present disclosure, the first driving wheel 133 and the second driving wheel 134 may be chain wheels, and the conveyor belt 135 may be a chain. Certainly, the present disclosure is not limited to the above two ways, any other way that can realize transmission may be suitable for the present disclosure.

In addition, in the present disclosure, the central frame 132 may set at least one group of drive unit. That is, one or more groups of drive units may be provided in the scanning bed control apparatus 1. When provided with multiple groups of drive units, the contact area between the conveyor belt 135 and the scanning bed 12 may be increased, so as to reduce local force of the conveyor belt 135. In this way, the gravity of the scanning bed 12 may be dispersed, so the transfer process may become smoother. In another example, with one group of drive unit, the width of the conveyor belt 135 may be adaptively increased, and thus may reduce local force of the conveyor belt 135.

As shown in FIGS. 1-3, in another aspect of this example, a medical imaging equipment may be provided. The medical imaging equipment may comprise an imaging device 2, a scanning bed 12 and a scanning bed control apparatus 1. The scanning bed control apparatus 1 may be used to control the scanning bed 12 to enter into a scanning area 21 of the imaging device 2. In particular, the scanning bed control apparatus 1 may control the scanning bed 12, thus achieving secondary transmission in the horizontal direction. In addition, the imaging device 2 may comprise a bed board support (not shown), so as to support the scanning bed 12 when the scanning bed 12 enters into the scanning area 21 of the imaging device 2, thereby ensuring that the force of the scanning bed 12 is balanced. As an example, the medical imaging equipment may be any one of MRI device, CT device, PET device, and X-ray imaging device. Of course, the scanning bed control apparatus 1 of this disclosure is not limited to the above devices, and it may be suitable for any other matched medical imaging equipment.

According to the drive mechanism of the scanning bed in the present disclosure, the scanning bed may reach the maximum stroke movement by two-stage drive. The drive mechanism is not only simple in structure and may reduce manufacturing cost, but also includes advantages of high transmission efficiency and transmission accuracy. In addition, without increasing length of the scanning bed, the movement scope of the scanning bed may increase through two-stage drive, so as to reduce the space occupied by the scanning bed effectively.

It should be understood that although the disclosure may adopt terms of the first and the second and so on to describe varieties of structures, these structures should not limited to these terms. These terms are only used to differentiate the same type of structure with each other. For example, without departing from the scope of the present disclosure, the first driving wheel may also be referred to as a second driving wheel. Similarly, the second driving wheel may also be referred to as a first driving wheel, depending on the context.

The above are only preferred examples of the present disclosure and are not intended to limit the disclosure within the spirit and principles of the present disclosure. Any changes made, equivalent replacement, or improvement in the protection of the present disclosure should contain within the range of the present disclosure.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product may be stored in a storage medium and may comprise a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention claimed is:

1. A scanning bed control apparatus, comprising:
a support table; and
a drive mechanism connected between the support table and a scanning bed, the drive mechanism comprises:
 a drive motor, wherein an output end of the drive motor is connected with a gear;
 a central frame, wherein a rack joggled with the gear is fixed on the central frame; and
 a drive unit, which is set on the central frame and comprises:
  a first driving wheel and a second driving wheel, which are set on two ends of the central frame respectively;
  a conveyor belt, which is sleeved on the first driving wheel and the second driving wheel;
  a first connector, which is set on an upper layer of the conveyor belt to connect with the scanning bed; and
  a second connector, which is set on a lower layer of the conveyor belt to connect with the support table;
 wherein, when the drive motor drives the central frame to move back and forth by joggling between the gear and the rack, the conveyor belt takes a connection site of the second connector and the support table as a fixed point and drives the scanning bed to move back and forth between the first driving wheel and the second driving wheel.

2. The scanning bed control apparatus according to claim 1, wherein,
the first driving wheel and the second driving wheel are synchronous pulleys,
the conveyor belt is a synchronous belt.

3. The scanning bed control apparatus according to claim 2, wherein the central frame is provided with at least one group of the drive unit.

4. The scanning bed control apparatus according to claim 1, wherein,
the first driving wheel and the second driving wheel are chain wheels,
the conveyor belt is a chain.

5. The scanning bed control apparatus according to claim 4, wherein the central frame is provided with at least one group of the drive unit.

6. The scanning bed control apparatus according to claim 1, wherein the drive motor is a combination of an electric motor and a speed reducer.

7. The scanning bed control apparatus according to claim 1, wherein,
when the scanning bed is at an initial position, the first connector is close to the first driving wheel, and the second connector is close to the second driving wheel;
when the scanning bed is at a maximum stroke position, the first connector is close to the second driving wheel, and the second connector is close to the first driving wheel.

8. The scanning bed control apparatus according to claim 1, wherein the drive motor is an electric motor.

9. A medical imaging equipment, comprising:
an imaging device,
a scanning bed, and
a scanning bed control apparatus, comprising:
 a support table; and
 a drive mechanism connected between the support table and the scanning bed, the drive mechanism comprising:
  a drive motor, wherein an output end of the drive motor is connected with a gear;
  a central frame, wherein a rack joggled with the gear is fixed on the central frame; and
  a drive unit, which is set on the central frame and comprises:
   a first driving wheel and a second driving wheel, which are set on two ends of the central frame respectively;
   a conveyor belt, which is sleeved on the first driving wheel and the second driving wheel;
   a first connector, which is set on an upper layer of the conveyor belt to connect with the scanning bed; and
   a second connector, which is set on a lower layer of the conveyor belt to connect with the support table;
 wherein, when the drive motor drives the central frame to move back and forth by joggling between the gear and the rack, the conveyor belt takes a connection site of the second connector and the support table as a fixed point and drives the scanning bed to move back and forth between the first driving wheel and the second driving wheel,
 wherein the scanning bed control apparatus controls the scanning bed entering into a scanning area of the imaging device.

10. The medical imaging equipment according to claim 9, wherein,
the first driving wheel and the second driving wheel are synchronous pulleys,
the conveyor belt is a synchronous belt.

11. The medical imaging equipment according to claim 10, wherein the central frame is provided with at least one group of the drive unit.

12. The medical imaging equipment according to claim 9, wherein,
the first driving wheel and the second driving wheel are chain wheels,
the conveyor belt is a chain.

13. The medical imaging equipment according to claim 12, wherein the central frame is provided with at least one group of the drive unit.

14. The medical imaging equipment according to claim 9, wherein the medical imaging equipment is provided with a bed board support internally to support the scanning bed.

15. The medical imaging equipment according to claim 9, wherein the medical imaging equipment is any one of magnetic resonance equipment, a computed tomography imaging device, a positron emission tomography imaging device, and an X-ray imaging device.

16. The medical imaging equipment according to claim 9, wherein,
 when the scanning bed is at an initial position, the first connector is close to the first driving wheel, and the second connector is close to the second driving wheel;
 when the scanning bed is at a maximum stroke position, the first connector is close to the second driving wheel, and the second connector is close to the first driving wheel.

17. The medical imaging equipment according to claim 9, wherein the drive motor is an electric motor.

18. The medical imaging equipment according to claim 9, wherein the drive motor is a combination of an electric motor and a speed reducer.

* * * * *